US008581581B2

(12) United States Patent
Machii et al.

(10) Patent No.: US 8,581,581 B2
(45) Date of Patent: Nov. 12, 2013

(54) MAGNETIC RESONANCE IMAGING APPARATUS AND MAGNETIC RESONANCE IMAGING METHOD

(71) Applicants: Yutaka Machii, Otawara (JP); Hiroshi Kusahara, Kyoto (JP); Yoshimori Kassai, Nasushiobara (JP)

(72) Inventors: Yutaka Machii, Otawara (JP); Hiroshi Kusahara, Kyoto (JP); Yoshimori Kassai, Nasushiobara (JP)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 0 days.

(21) Appl. No.: 13/623,920

(22) Filed: Sep. 21, 2012

(65) Prior Publication Data
US 2013/0015855 A1    Jan. 17, 2013

Related U.S. Application Data

(63) Continuation of application No. PCT/JP2011/079413, filed on Dec. 19, 2011.

(30) Foreign Application Priority Data

Jan. 11, 2011   (JP) .................................. 2011-003509

(51) Int. Cl.
*G01V 3/00*   (2006.01)
(52) U.S. Cl.
USPC .......................................... 324/307; 324/309
(58) Field of Classification Search
USPC .......................................... 324/307, 309, 314
See application file for complete search history.

(56) References Cited

U.S. PATENT DOCUMENTS

| 6,815,952 | B1 * | 11/2004 | Rose et al. ................... 324/307 |
| 6,969,991 | B2 * | 11/2005 | Bammer et al. ............. 324/307 |
| 8,283,925 | B2 * | 10/2012 | Auslender et al. ........... 324/309 |
| 2011/0304334 | A1 * | 12/2011 | Feiweier ...................... 324/314 |

FOREIGN PATENT DOCUMENTS

| JP | 2007-159718 | 6/2007 |
| JP | 2009-195584 | 9/2009 |

OTHER PUBLICATIONS

International Search Report for PCT/JP2011/079413, mailed Feb. 7, 2012.
Written Opinion for PCT/JP2011/079413, mailed Feb. 7, 2012.
Hansson et al., "A Novel Robust Algorithm to Correct for Eddy Current Distortions in High B-Value Diffusion MRI", *Proceedings of ISMRM-ESMRMB—Joint Annual Meeting*, 2010, 05. #1627.
Notification of Transmittal of Copies of Translation of the International Preliminary Report on Patentability in PCT/JP2011/079413 mailed Jul. 25, 2013.

* cited by examiner

*Primary Examiner* — Louis Arana
(74) *Attorney, Agent, or Firm* — Nixon & Vanderhye PC

(57) ABSTRACT

According to one embodiment, a magnetic resonance imaging apparatus includes an imaging unit and a strain correction unit. The imaging unit is configured to acquire frames of diffusion weighted image data corresponding to different b-values by diffusion weighted imaging with applying MPG pulses corresponding to the different b-values of which application axes are same. The strain correction unit is configured to calculate a strain correction coefficient for diffusion weighted image data to be a target of a strain correction based on diffusion weighted image data corresponding to a b-value different from a b-value corresponding to the diffusion weighted image data to be the target of the strain correction among the frames of the diffusion weighted image data to generate image data after the strain correction by the strain correction of the diffusion weighted image data to be the target of the strain correction using the calculated strain correction coefficient.

12 Claims, 9 Drawing Sheets

MAGNETIC RESONANCE IMAGING APPARATUS AND MAGNETIC RESONANCE IMAGING METHOD

CROSS REFERENCE TO RELATED APPLICATIONS

This is a continuation of Application PCT/JP2011/079413, filed Dec. 19, 2011.

This application is based upon and claims the benefit of priority from Japanese Patent Application No. 2011-003509, filed Jan. 11, 2011; the entire contents of which are incorporated herein by reference.

FIELD

Embodiments described herein relate generally to a MRI (magnetic resonance imaging) apparatus and a magnetic resonance imaging method.

BACKGROUND

MRI is an imaging method which excites nuclear spin of an object set in a static magnetic field with a RF (radio frequency) signal having the Larmor frequency magnetically and reconstructs an image based on MR (magnetic resonance) signals generated due to the excitation.

In the field of magnetic resonance imaging, there is an imaging method called echo planar imaging (EPI). EPI is one of the high speed imaging methods in MRI. EPI is an imaging method for performing a scan which inverts a gradient magnetic field with high speed continuously after a single nuclear magnetic excitation so as to generate echoes continuously. More specifically, in EPI, all the data necessary for image reconstruction are acquired by generating continuous gradient echoes by steps of phase encodes (PE) before a magnetization in a x-y plane attenuates and disappears by transverse relaxation (T2 relaxation) after applying an excitation pulse (FLIP PULSE). EPI includes SE EPI with using a spin echo (SE) method to acquire spin echo signals generated after an excitation pulse and a refocus pulse (FLOP PULSE), FE EPI with using a field echo (FE) method to acquire echo signals generated after applying an excitation pulse and FFE EPI using a FFE (Fast FE) method. While using EPI to generate data for a single image with combined echo train data obtained by applying an excitation pulse plural times is called multi shot EPI; EPI to reconstruct an image by applying only a single excitation pulse is called single shot (SS) EPI. In addition, there is EPI referred to as Hybrid EPI.

Further, as an applied technology in EPI, DWI (diffusion weighted imaging) is known. DWI is an imaging method for enhancing phase shifts due to motions of imaging targets by applying gradient magnetic fields having strong intensities referred to as MPG (motion probing gradient) pulses to acquire images in which a diffusion effect in the imaging targets is enhanced. Generally, parameter images such as ADC (Apparent Diffusion Coefficient) images and/or isotropic DWIs (diffusion weighted images) are generated for diagnosis based on DWIs acquired by changing an application direction of MPG pulses and a reference image acquired by applying no MPG pulse.

Furthermore, DTI (diffusion tensor imaging) is known as an application in DWI. Generally, DTI is an imaging method for acquiring DWIs by changing an application direction of MPG pulses to image an imaging part mathematically using a tensor analysis based on the DWIs.

In EPI used for DWI and DTI, eddy currents are induced due to MPG pulses having strong intensities. Accordingly, a strain sometimes occurs in an image due to an influence of nonuniform magnetic fields by eddy currents. The strain in an image depends on application timings, intensities and directions of MPG pulses.

Therefore, positional shifts due to image strains according to conditions of MPG pulses may occur between a reference image acquired without applying any MPG pulse and a DWI as well as between DWIs acquired with changing application directions and intensities of MPG pulses. Generating ADC images based on images having such positional shifts causes artifacts and leads to reduced resolution. Alternatively, generating isotropic DWIs based on images having strains results in blurry images. In DTI, mutually different strains are also generated in images acquired with changing application directions of MPG pulses. Consequently, it may become difficult to perform a precise tensor analysis.

Under such background, various techniques for correcting a strain of an image due to MPG pulses in an image space are devised.

In DWI and DTI, it is an object to correct a strain in an image more satisfactorily.

It is an object of the present invention to provide a magnetic resonance imaging apparatus and a magnetic resonance imaging method which can obtain a DWI or a DTI of which strain is corrected more satisfactorily.

DETAILED DESCRIPTION

According to one embodiment, a magnetic resonance imaging apparatus includes an imaging unit and a strain correction unit. The imaging unit is configured to acquire frames of diffusion weighted image data corresponding to different b-values by diffusion weighted imaging with applying MPG pulses corresponding to the different b-values of which application axes are same. The strain correction unit is configured to calculate a strain correction coefficient for diffusion weighted image data to be a target of a strain correction based on diffusion weighted image data corresponding to a b-value different from a b-value corresponding to the diffusion weighted image data to be the target of the strain correction among the frames of the diffusion weighted image data to generate image data after the strain correction by the strain correction of the diffusion weighted image data to be the target of the strain correction using the calculated strain correction coefficient.

According to another embodiment, a magnetic resonance imaging method includes: acquiring frames of diffusion weighted image data corresponding to different b-values by diffusion weighted imaging with applying MPG pulses corresponding to the different b-values of which application axes are same; and calculating a strain correction coefficient for diffusion weighted image data to be a target of a strain correction based on diffusion weighted image data corresponding to a b-value different from a b-value corresponding to the diffusion weighted image data to be the target of the strain correction among the frames of the diffusion weighted image data to generate image data after the strain correction by the strain correction of the diffusion weighted image data to be the target of the strain correction using the calculated strain correction coefficient.

A magnetic resonance imaging apparatus and a magnetic resonance imaging method according to embodiments of the present invention will be described with reference to the accompanying drawings.

Figure 1:
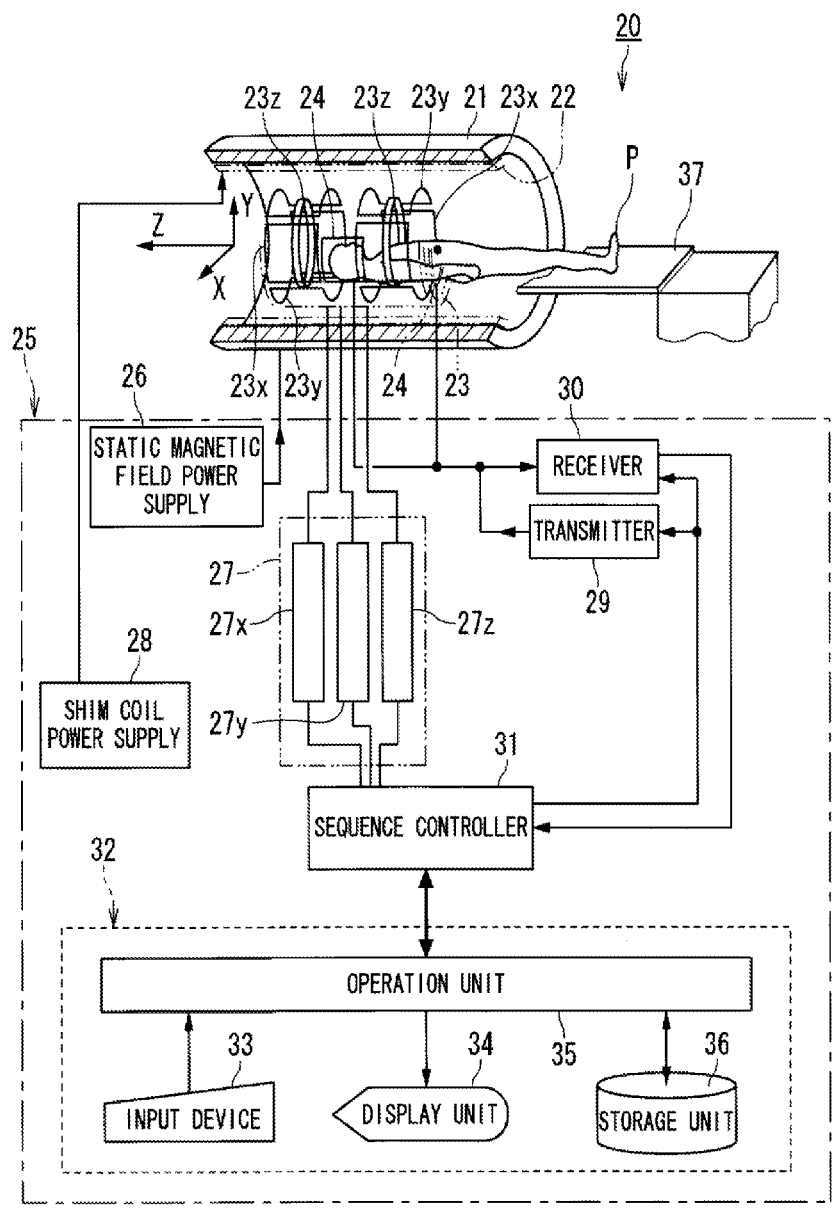
FIG. 1 is a block diagram showing a magnetic resonance imaging apparatus according to an embodiment of the present invention.

FIG. 1 is a block diagram showing a magnetic resonance imaging apparatus according to an embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil 23 and RF coils 24.

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a display unit 34, a operation unit 35 and a storage unit 36.

The static field magnet 21 communicates with the static magnetic field power supply 26. The static magnetic field power supply 26 supplies electric current to the static field magnet 21 to get the function to generate a static magnetic field in a imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z which is cylinder-shaped is arranged inside the static field magnet 21. The gradient coil 23 has also a bed 37 in the area formed inside it which is an imaging area. The bed 37 supports an object P. The RF coils 24 include a whole body coil (WBC: whole body coil), which is built in the gantry, for transmission and reception of RF signals and local coils, which are arranged around the bed 37 or the object P, for reception of RF signals.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil 23x, the Y-axis gradient coil 23y and the Z-axis gradient coil 23z respectively so as to generate gradient magnetic fields Gx, Gy and Gz in the X, Y and Z directions in the imaging area.

The RF coils 24 communicate with the transmitter 29 and/or the receiver 30. The transmission RF coil 24 has a function to transmit a RF signal given from the transmitter 29 to the object P. The reception RF coil 24 has a function to receive a MR signal generated due to an nuclear spin inside the object P which is excited by the RF signal to give to the receiver 30.

The sequence controller 31 of the control system 25 communicates with the gradient power supply 27, the transmitter 29 and the receiver 30. The sequence controller 31 has a function to storage sequence information describing control information needed in order to make the gradient power supply 27, the transmitter 29 and the receiver 30 drive and generate gradient magnetic fields Gx, Gy and Gz in the X, Y and Z directions and a RF signal by driving the gradient power supply 27, the transmitter 29 and the receiver 30 according to a predetermined sequence stored. The control information above-described includes motion control information, such as intensity, impression period and impression timing of the pulse electric current which should be impressed to the gradient power supply 27.

The sequence controller 31 is also configured to give raw data to the computer 32. The raw data is complex data obtained through the detection of a MR signal and A/D (analog to digital) conversion to the MR signal detected in the receiver 30.

The transmitter 29 has a function to give a RF signal to the RF coil 24 in accordance with control information provided from the sequence controller 31. The receiver 30 has a function to generate raw data which is digitized complex number data by detecting a MR signal given from the RF coil 24 and performing predetermined signal processing and A/D converting to the MR signal detected. The receiver 30 also has a function to give the generated raw data to the sequence controller 31.

The computer 32 gets various functions by the operation unit 35 executing some programs stored in the storage unit 36 of the computer 32. Alternatively, some specific circuits having various functions may be provided with the magnetic resonance imaging apparatus 20 instead of using at least some of the programs.

Figure 2:
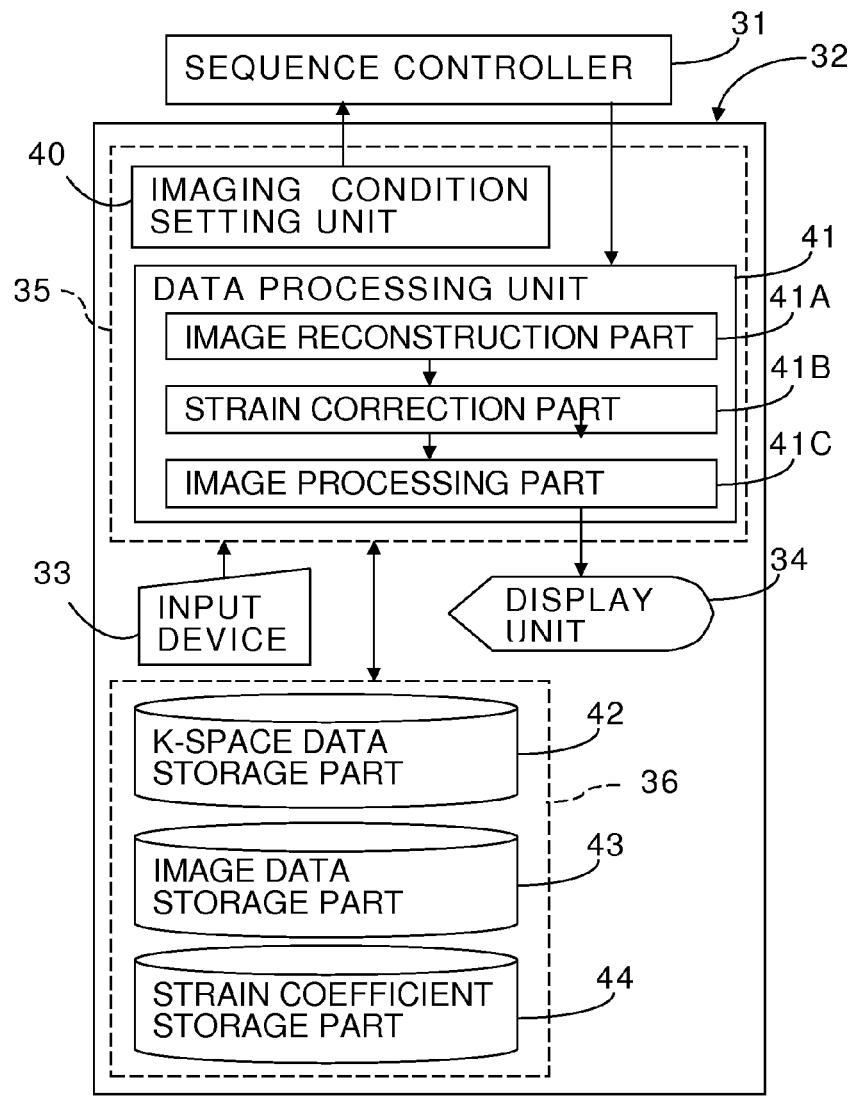
FIG. 2 is a functional block diagram of the computer shown in FIG. 1.

FIG. 2 is a functional block diagram of the computer 32 shown in FIG. 1.

The operation unit 35 of the computer 32 functions as an imaging condition setting unit 40 and a data processing unit 41 by executing the programs stored in the storage unit 36. The data processing unit 41 has an image reconstruction part 41A, a strain correction part 41B and an image processing part 41C. Further, the storage unit 36 functions as a k-space data storage part 42, an image data storage part 43 and a strain coefficient storage part 44.

The imaging condition setting unit 40 has a function to set imaging conditions including an EPI sequence based on information inputted from the input device 33 and supply the set imaging conditions to the sequence controller 31 to control a drive of the sequence controller 31.

Figure 3:
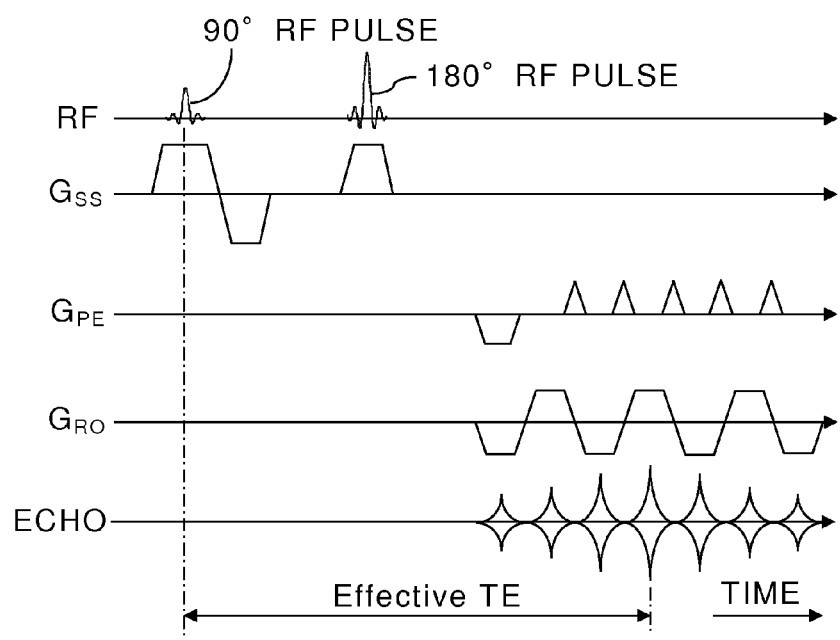
FIG. 3 is a chart showing an example of EPI sequence set in the imaging condition setting unit shown in FIG. 2.

FIG. 3 is a chart showing an example of EPI sequence set in the imaging condition setting unit 40 shown in FIG. 2.

In FIG. 3, the abscissa axis denotes time, RF denotes PF transmission pulses, $G_{SS}$ denotes SS (slice selection) gradient pulses, $G_{PE}$ denotes PE (phase encode) gradient pulses, $G_{RO}$ denotes RO (readout) gradient pulses and ECHO denotes MR reception echo signals respectively.

As shown in FIG. 3, an EPI sequence is a pulse sequence for applying a 90 degree pulse and a 180 degree pulse to excite a slice selected by applying a SS gradient magnetic field pulse and subsequently applying PE gradient magnetic field pulses and RO gradient magnetic field pulses repeatedly to acquire MR reception echo signals continuously from the selected slice. A period from an applying time of the 90 degree RF pulse to an acquisition time of an echo signal at the center of k-space is referred to as an effective TE (effective echo time).

In addition, the imaging condition setting unit 40 has a function to set a pulse sequence to perform DWI with setting a b-factor, which is an index for an effectiveness of a MPG pulse, to different values. More specifically, in the imaging condition setting unit 40, imaging conditions to acquire frames of DWI data corresponding to mutually different b-values can be set. Especially, the imaging condition setting unit 40 also has a function to set two DWI sequences with applying MPG pulses of which application axes and absolute values of the b-values are mutually same and of which polarities are mutually different.

Figure 4:
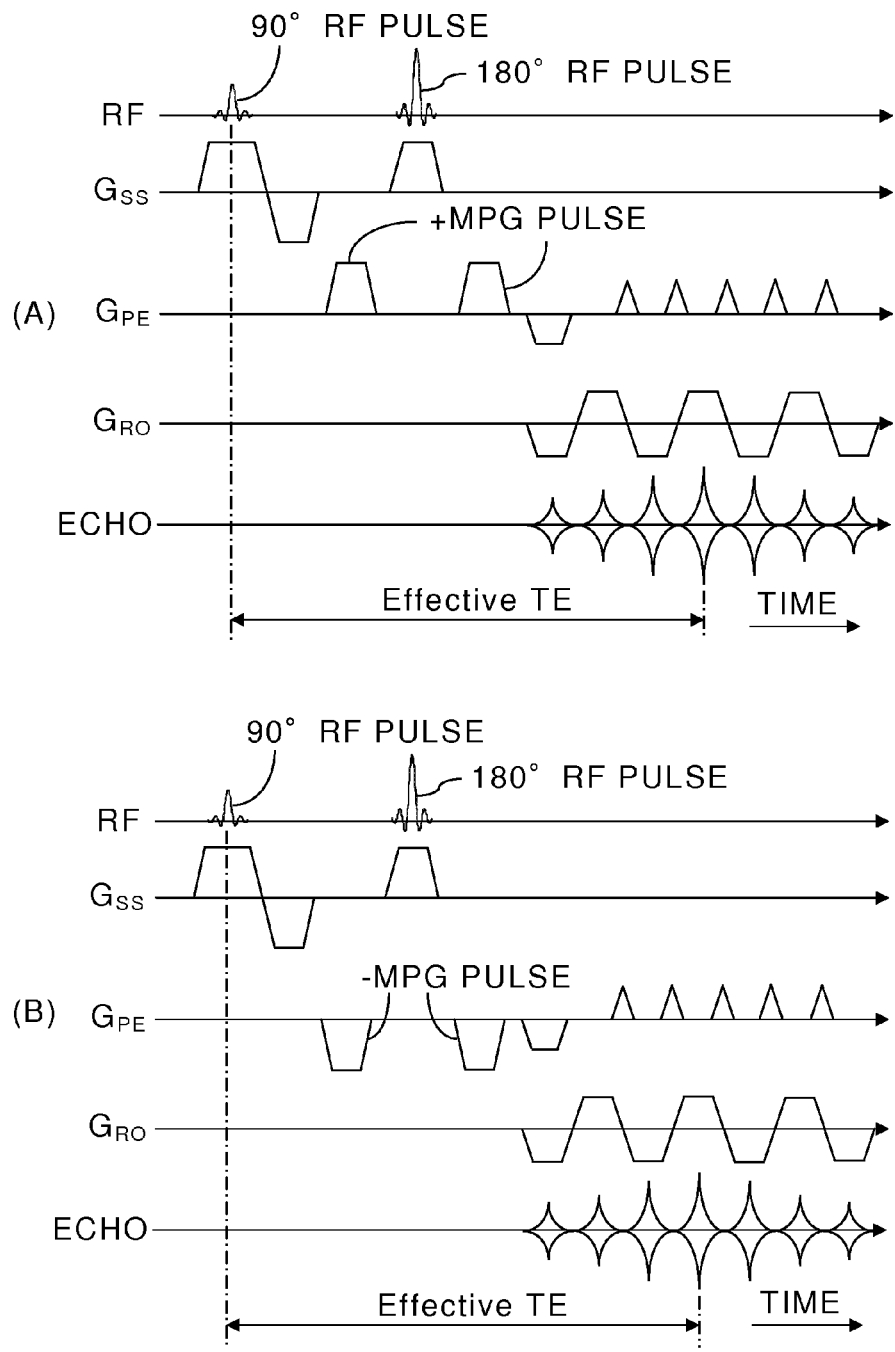
FIG. 4 is a chart showing an example of two EPI sequences set in the imaging condition setting unit shown in FIG. 2.

FIG. 4 is a chart showing an example of two EPI sequences set in the imaging condition setting unit 40 shown in FIG. 2.

In each of (A) and (B) of FIG. 4, the abscissa axis denotes time, RF denotes PF transmission pulses, $G_{SS}$ denotes SS gradient pulses, $G_{PE}$ denotes PE gradient pulses, $G_{RO}$ denotes RO gradient pulses and ECHO denotes MR reception echo signals respectively.

FIG. 4(A) shows an example of a DWI sequence with applying MPG pulses of which polarities are positive and application axes are in a PE direction. Meanwhile, FIG. 4(B) shows an example of a DWI sequence with applying MPG pulses of which polarities are negative and application axes are in a PE direction. As shown on (A) and (B) of FIG. 4, two DWI sequences with applying the MGP pulses (+MPG PULSE, −MPG PULSE), of which polarities are positive and negative respectively, application axes are same and areas are same, prior to acquiring MR reception echo signals, i.e., applying the PE gradient magnetic field pulses can be set as imaging conditions in the imaging condition setting unit 40.

Note that, FIGS. 4 (A) and (B) show examples of MPG pulses of which application axes are in the PE direction. However, another direction may be set to an application axis according to a purpose in diagnosis.

In addition, DWI data can be acquired as AVERAGE image data by averaging processing which averages multiple frames of imaging data. By averaging processing, DWI data improved in SNR (signal to noise ratio) can be acquired. Therefore, an AVERAGE number which is the number of frames of image data added for averaging, application axes of MPG pulses corresponding to frames of DWI data to be added and b-values of DWI data to be added are set as imaging conditions in the imaging condition setting unit 40.

The data processing unit 41 has a function to acquire MR signals from the sequence controller 31 to arrange the acquired MR signals in the k-space formed in the k-space data storage part 42 as k-space data, a function to generate image data after a strain correction by data processing including image reconstruction processing and strain correction processing of k-space data stored in the k-space data storage part 42, a function to write the generated image data in the image data storage part 43, a function to obtain strain correction coefficients used for strain corrections of DWI data to write them in the strain coefficient storage part 44 and a function to display image data on the display unit 34.

The image reconstruction part 41A has a function to reconstruct image data by image reconstruction processing including FT (Fourier transform) of k-space data read from the k-space data storage part 42. The image data acquired with applying at least one MPG pulse is DWI data. Each frame of DWI data is image data corresponding to a b-value and an application direction of a MPG pulse or MPG pulses. Note that, image data which is not DWI data corresponds to image data of which b-value is zero.

Further, the image reconstruction part 41A has a function to generate AVERAGE image data by the first averaging processing for averaging frames of DWI data acquired with setting the same application axis and the same b-value to MPG pulses, as needed. Specifically, a SNR in DWI data corresponding to a specific application axis and b-value can be improved by adding frames of DWI data acquired under same conditions for DWI.

The strain correction part 41B has a function to acquire strain correction coefficients to conduct strain correction for DWI data acquired with applying MPG pulses. The strain correction part 41B also has a function to generate image data after strain correction by the strain correction of DWI data, which is a target of the strain correction, using the acquired strain correction coefficients or strain correction coefficients acquired with referring to the strain coefficient storage part 44.

Especially, the strain correction part 41B is configured to calculate a strain correction coefficient corresponding to DWI data to be a target of strain correction, based on DWI data corresponding to a b-value different from one corresponding to the DWI data to be the target of the strain correction among frames of DWI data acquired by DWI. Calculating a strain correction coefficient can be also performed based on image data, which is not DWI data, acquired with setting a b-value to zero without applying MPG pulses, as needed.

More specifically, based on two frames of DWI data corresponding to MPG pulses of which application axes and absolute values of b-values are mutually same and of which polarities are mutually different, a stain correction coefficient corresponding to one of the two DWI data can be obtained with a higher accuracy.

Figure 5:
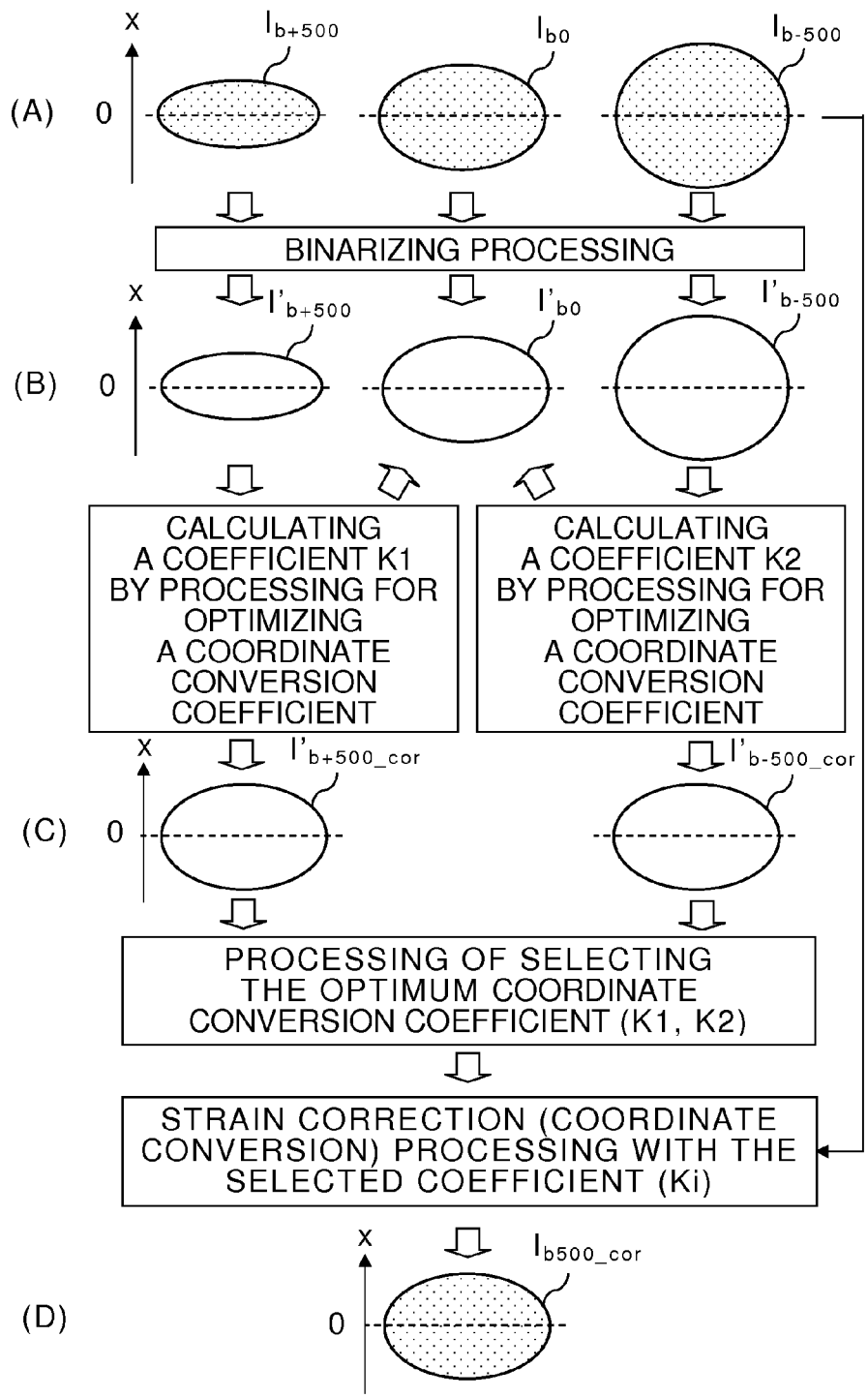
FIG. 5 is a diagram explaining the first method for obtaining a strain correction coefficient to perform a strain correction in the strain correction part shown in FIG. 2.

FIG. 5 is a diagram explaining the first method for obtaining a strain correction coefficient to perform a strain correction in the strain correction part 41B shown in FIG. 2.

In (A), (B), (C) and (D) of FIG. 5, each ordinate axis donates x-axis. For example, when frames of image data are acquired with setting b-values to 0, +500 and −500 respectively, a reference image data $I_{b0}$ acquired with setting the b-value to zero ideally becomes image data having no stain because of no influence from MPG pulses as shown in FIG. 5 (A). In contrast, DWI data $I_{b+500}$ corresponding to the b-value of +500 and DWI data $I_{b-500}$ corresponding to the b-value of −500 become image data having strain under influences from MPG pulses respectively.

The DWI data $I_{b+500}$ corresponding to the b-value of +500 and the DWI data $I_{b-500}$ corresponding to the b-value of −500 are influenced on the MPG pulses having the mutually opposite polarities. Therefore, the polarities of the strain directions become mutually symmetric with regard to the origin as long as the other influences are negligible. Note that, FIG. 5 (A) shows an example case of one dimensional strain toward the x axis direction in the DWI data $I_{b+500}$ and the DWI data $I_{b-500}$ respectively for the sake of simplifying an explanation. Not only cases in which b-values are ±500, two frames of DWI data corresponding to b-values having a same absolute values and the opposite signs show a same strain quantity and become mutually symmetric strain directions with regard to the origin as long as the other influences are negligible.

By binarizing processing using a threshold value to the respective frames of image data $I_{b0}$, $I_{b+500}$ and $I_{b-500}$ corresponding to the b-values of 0, +500 and −500 as described above, frames of binarized image data $I'_{b0}$, $I'_{b+500}$ and $I'_{b-500}$ corresponding to the b-values of 0, +500 and −500 respectively are generated as shown in FIG. 5 (B).

Next, a sum of square differences between pixel values at respective image points of the binarized reference image data $I'_{b0}$ corresponding to the b-value of 0 and those of the binarized DWI data $I'_{b+500}$ corresponding to the b-value of +500 is calculated with shifting the respective image points of the binarized DWI data $I'_{b+500}$ corresponding to the b-value of +500 by coordinate conversion. That is, optimizing processing for minimizing a square error in the pixel values of the binarized DWI data $I'_{b+500}$ from the binarized reference image data $I'_{b0}$ is performed using respective coefficients expressing the coordinate conversion of the binarized DWI data $I'_{b+500}$ as parameters.

Using an affine transformation expressed by a combination of a parallel translation, a rotational movement, expansion and contraction for the coordinate conversion leads to simplify processing. The coordinate conversion under the affine transformation is expressed by the expression (1).

$$f(x, y, z) = \begin{bmatrix} x' \\ y' \\ z' \end{bmatrix} = \begin{bmatrix} p_0 & p_1 & p_2 \\ p_3 & p_4 & p_5 \\ p_6 & p_7 & p_8 \end{bmatrix} \begin{bmatrix} x \\ y \\ z \end{bmatrix} + \begin{bmatrix} T_x \\ T_y \\ T_z \end{bmatrix} \quad (1)$$

Note that, in the expression (1), the f denotes a function expressing the coordinate conversion, (x, y, z) denotes a spatial coordinate of image points before the coordinate conversion, (x', y', z') denotes a spatial coordinate of image points after the coordinate conversion and p0, p1, p2, . . . , p8, Tx, Ty and Tz denote coefficients of the coordinate conversion.

When optimizing processing to minimize the square error in the pixel values of the binarized DWI data $I'_{b+500}$ is performed using each coordinate conversion coefficient as a parameter in the expression (1), binarized corrected DWI data $I'_{b+500\_cor}$ which has the smallest position gap from the binarized reference image data $I'_{b0}$ can be generated as shown in FIG. (5) and coordinate conversion coefficients can be acquired as a matrix. Specifically, a combination K1 of the coordinate conversion coefficients minimizing the sum of differences of the respective pixel values after the coordinate conversion processing and the binarizing processing between the reference image data $I_{b0}$ and the DWI data $I_{b+500}$ corresponding to the positive b-value can be obtained. Note that, the optimizing processing includes sequential processing for searching coordinate conversion coefficients and interpolation processing of pixel values.

In a similar manner, a combination K2 and binarized corrected DWI data $I'_{b-500\_cor}$ can be acquired. The combination K2 is a combination of coordinate conversion coefficients minimizing the sum of differences of the respective pixel values after the coordinate conversion processing and the binarizing processing between the reference image data $I_{b0}$ and the DWI data $I_{b-500}$ corresponding to the negative b-value.

Then, a combination (K1 or K2) of coordinate conversion coefficients, used for generating the binarized corrected DWI data ($I'_{b+500\_cor}$ or $I'_{b-500\_cor}$), corresponding to the smaller sum of square differences in pixel values from the binarized reference image data $I'_{b0}$ can be selected and adopted as strain correction coefficients.

In addition, by coordinate conversion of the DWI data ($I_{b+500}$ or $I_{b-500}$), for generating the binarized correction DWI data ($I'_{b+500\_cor}$ or $I'_{b-500\_cor}$) corresponding to the smaller sum of the square differences in pixel values from the binarized reference image data $I'_{b0}$, with the strain correction coefficients, DWI data $I_{b500\_cor}$ after strain correction can be acquired as shown in FIG. 5 (D).

Figure 6:
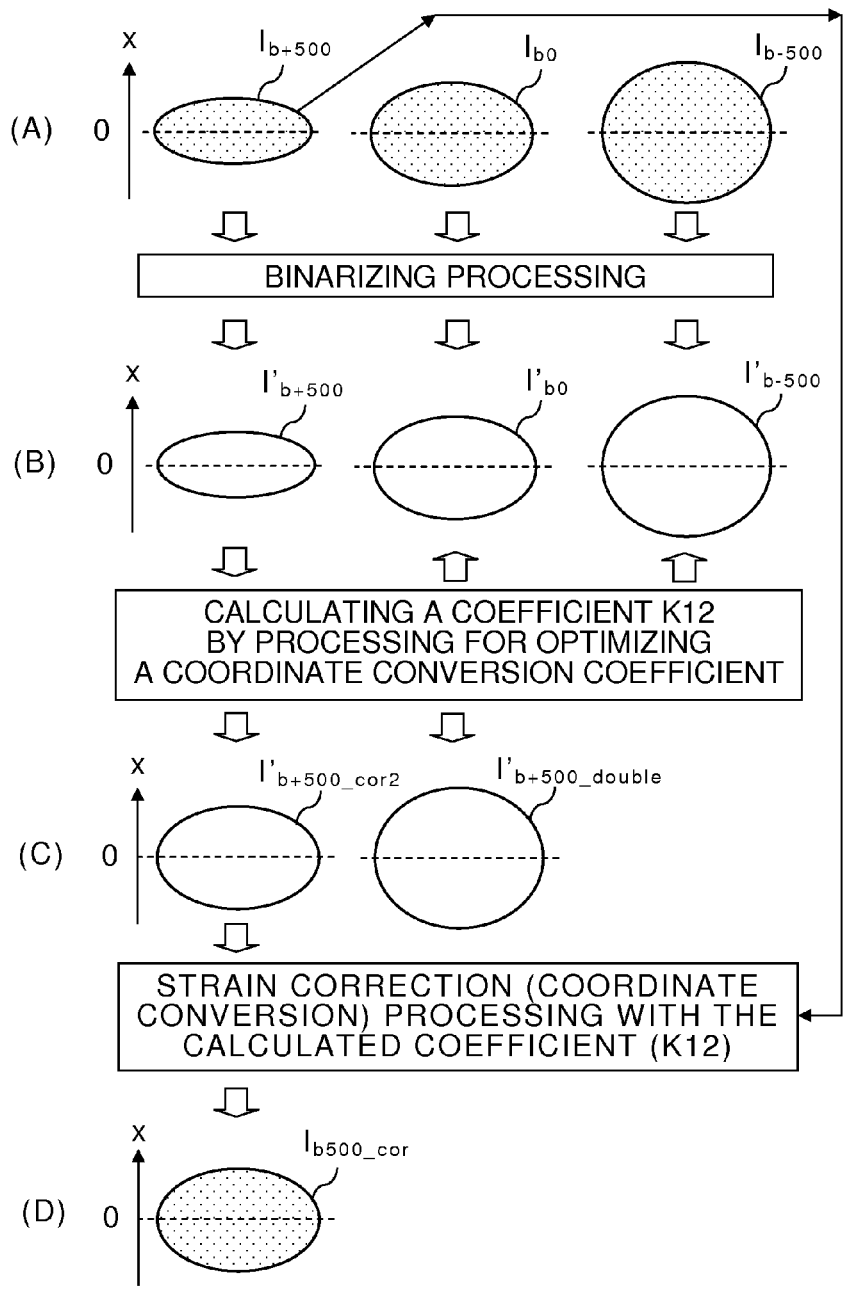
FIG. 6 is a diagram explaining the second method for obtaining a strain correction coefficient to perform a strain correction in the strain correction part shown in FIG. 2.

FIG. 6 is a diagram explaining the second method for obtaining a strain correction coefficient to perform a strain correction in the strain correction part 41B shown in FIG. 2.

In (A), (B), (C) and (D) of FIG. 6, each ordinate axis denotes x-axis. Similarly to (A) and (B) of FIG. 5, frames of binarized image data $I'_{b0}$, $I'_{b+500}$ and $I'_{b-500}$ corresponding to the b-values of 0, +500 and −500 respectively can be generated as shown in FIG. 6 (B) by acquisition and binarizing processing of reference image data $I_{b0}$ having no strain and two frames of DWI data $I_{b+500}$ and $I_{b-500}$ corresponding to the b-values of .+−0.500 and having mutually opposite strain directions as shown in FIG. 6 (A).

Here, using a coordinate conversion coefficient combination 2*K1, derived by duplicating the respective optimized coordinate conversion coefficients minimizing the sum of square differences in pixel values of the binarized DWI data $I'_{b+500}$ corresponding to the b-value of +500 from the binarized reference image data $I'_{b0}$, for the coordinate conversion of the binarized DWI data $I'_{b+500}$ corresponding to the b-value of +500 is assumed. Then, binarized conversion DWI data $I'_{b+500\_double}$ generated by the coordinate conversion becomes equal to the binarized DWI data $I'_{b-500}$ corresponding to the b-value of −500 logically.

Accordingly, optimizing processing for minimizing the total amount of SumError1+SumError2 is performed with setting the respective coordinate conversion coefficients of the binarized DWI data $I'_{b+500}$ corresponding to the b-value of +500 as parameters. The SumError1 is the sum of square differences in pixel values of the binarized DWI data $I'_{b+500}$ corresponding to the b-value of +500 from the binarized reference image data $I'_{b0}$. The SumError2 is the sum of square differences in pixel values between the binarized transformed DWI data $I'_{b+500\_double}$ derived by coordinate conversion with the combination of duplicated coordinate conversion coefficients and the binarized DWI data $I'_{b-500}$ corresponding to the b-value of −500.

As a result of the optimizing processing, binarized correction DWI data $I'_{b+500\_cor2}$ and binarized conversion DWI data $I'_{b+500\_double}$ are generated as shown in FIG. 6 (C). In addition, a combination K12 of coordinate conversion coefficients can be acquired. The combination K12 is the combination of coordinate conversion coefficients which minimize both a position gap between the binarized DWI data $I'_{b+500}$ corresponding to the b-value of +500 and the binarized reference image data $I'_{b0}$ corresponding to the b-value of 0 and a substantial position gap between the binarized DWI data $I'_{b+500}$ corresponding to the b-value of +500 and the binarized DWI data I'$_{b-500}$ corresponding to the b-value of −500.

Then, the acquired coordinate conversion coefficient combination K12 can be set as strain correction coefficients for the DWI data I$_{b+500}$ corresponding to the b-value of +500. Further, by coordinate conversion of the DWI data I$_{b+500}$ corresponding to the b-value of +500 using the coordinate conversion coefficients, DWI data I$_{b500\_cor}$ after the strain correction can be acquired as shown in FIG. 6 (D).

Note that, in the example described above, the case of processing for optimizing the respective coordinate conversion coefficients of the binarized DWI data I'$_{b+500}$ corresponding to the b-value of +500 as parameters has been explained. In a similar manner, the strain correction coefficients can be also acquired by processing for optimizing the respective coordinate conversion coefficients of the binarized DWI data I'$_{b-500}$ corresponding to the b-value of −500 as parameters.

In addition, the strain correction coefficients can be obtained without the image data of which b-value is zero.

Figure 7:
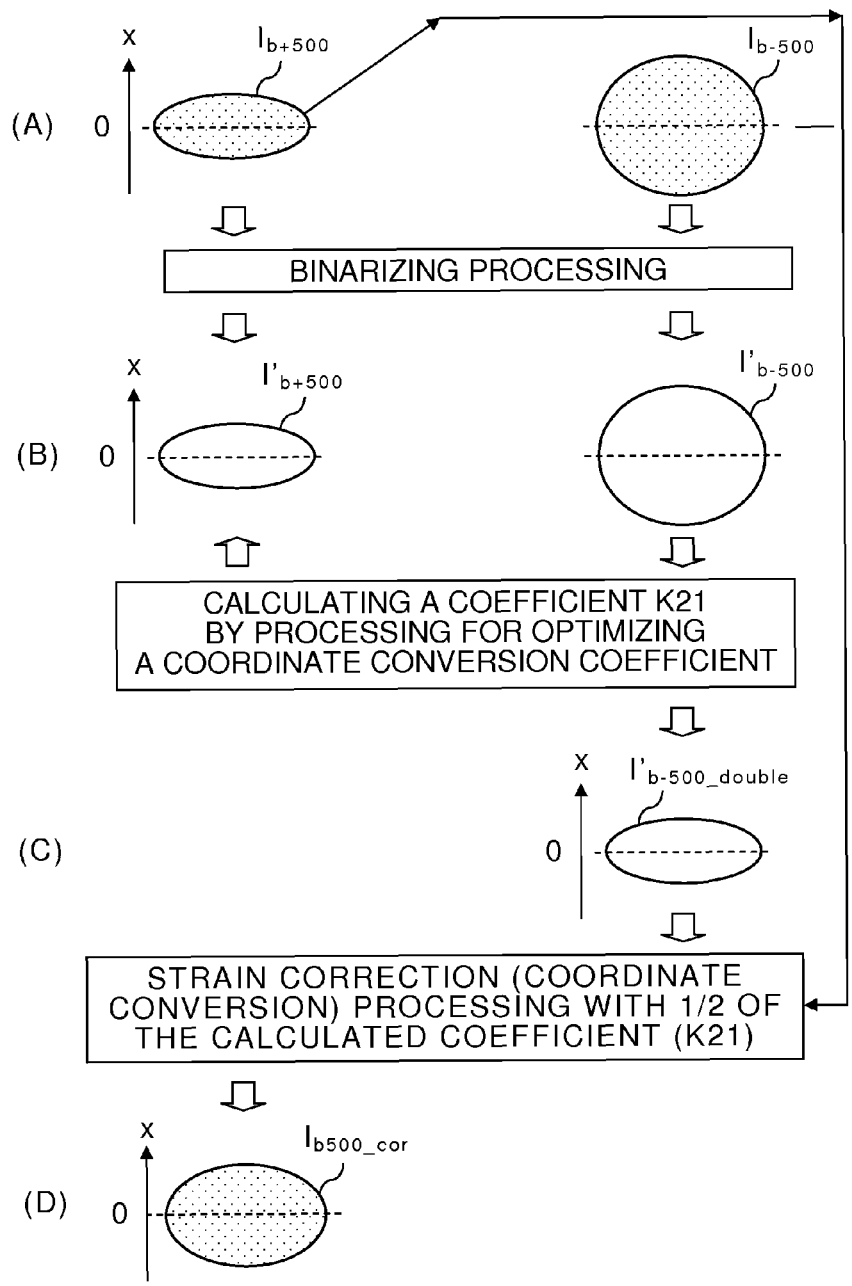
FIG. 7 is a diagram explaining the third method for obtaining a strain correction coefficient to perform a strain correction in the strain correction part shown in FIG. 2.

FIG. 7 is a diagram explaining the third method for obtaining a strain correction coefficient to perform a strain correction in the strain correction part 41B shown in FIG. 2.

In (A), (B), (C) and (D) of FIG. 7, each ordinate axis denotes x-axis. Similarly to (A) and (B) of FIG. 5, frames of binarized image data I'$_{b+500}$ and I'$_{b-500}$ corresponding to the b-values of +500 and −500 respectively can be generated as shown in FIG. 7 (B) by acquisition and binarizing processing of two frames of DWI data I$_{b+500}$ and I$_{b-500}$ corresponding to the b-values of +500 and −500 and having mutually opposite strain directions as shown in FIG. 7 (A).

Next, optimizing processing for minimizing the sum of square differences in pixel values between the binarized DWI data I'$_{b+500}$ corresponding to the b-value of +500 and the binarized DWI data I'$_{b-500}$ corresponding to the b-value of −500 is performed using respective coordinate conversion coefficients of the binarized image data I'$_{b-500}$ corresponding to the b-value of −500 as parameters.

As a result of the optimizing processing, binarized transformed DWI data I'$_{b-500\_double}$ after the coordinate conversion of the binarized image data I$_{b-500}$ corresponding to the b-value of −500 is generated as shown in FIG. 7 (C). In addition, a combination K21 of coordination conversion coefficients can be acquired. The combination K21 of the coordination conversion coefficients is a combination which minimizes a substantial position gap between the binarized DWI data I'$_{b+500}$ corresponding to the b-value of +500 and the binarized DWI data I'$_{b-500}$ corresponding to the b-value of −500.

Then, the combination K12 of the respective coordinate conversion coefficients used to generate the binarized transformed DWI data I'$_{b-500\_double}$ corresponds to twice coordinate conversion coefficients optimum for minimizing the sum of square differences in pixel values of the binarized DWI data I'$_{b+500}$ corresponding to the b-value of +500 from the binarized reference image data I'$_{b0}$.

For that reason, a combination (K21)/2 of coordinate conversion coefficients which corresponds the half of the respective coordinate conversion coefficients used to generate the binarized transformed DWI data I'$_{b-500\_double}$ can be set as strain correction coefficients for the DWI data I$_{b+500}$ corresponding to the b-value of +500. In addition, by coordinate conversion of the DWI data I$_{b+500}$ corresponding to the b-value of +500 using the strain correction coefficients, DWI data I$_{b500\_cor}$ after strain correction can be acquired as shown in FIG. 7 (D).

Note that, in the first, the second and the third ways shown in FIGS. 5, 6 and 7, the sum of square differences in pixel values has been set as the target for optimizing processing. However, another index such as a correlation coefficient representing a position gap between two frames of binarized image data may be the target for optimizing processing. Further, optimizing processing for minimizing an index of position gap between two frames of image data may be performed using the coordinate conversion coefficients for the DWI data I$_{b+500}$ or I$_{b-500}$ as parameters without binarizing processing as edge detection processing.

Alternatively, respective edges may be detected from frames of image data including DWI data by arbitrary edge detection processing with or without binarizing processing to perform optimizing processing for minimizing an index representing a position gap between the detected edges. Then, strain correction coefficients can be calculated by processing including edge detection for the two frames of DWI data.

Accordingly, the first way shown in FIG. 5 can be expressed as the way in which respective coordinate conversion coefficients for the two frames of DWI data or two frames of image data generated based on the two frames of DWI data are calculated by optimizing processing for minimizing an index of a position gap of each of the two frames of DWI data or each of the two frames of the image data from image data acquired with setting a b-value to zero to adopt a coordinate conversion coefficient corresponding to the smaller index as the strain correction coefficient. In this way, the respective coordinate conversion coefficients are used as parameters for the optimizing processing.

Further, the second way shown in FIG. 6 can be expressed as the way in which the strain correction coefficient is determined based on a coordinate conversion coefficient for one of the two frames of the DWI data or one of two frames of image data generated based on the two frames of DWI data. In this way, the coordinate conversion coefficient is calculated by optimizing processing for minimizing an index of a position gap of the one of the two frames of DWI data or the one of the two frames of the image data from image data acquired with setting a b-value to zero and an index of a position gap of that from the other using the coordinate conversion coefficient as a parameter.

Further, the third way shown in FIG. 7 can be expressed as the way in which the strain correction coefficient is determined based on a coordinate conversion coefficient for one of the two frames of DWI data or one of two frames of image data generated based on the two frames of DWI data. In this way, the coordinate conversion coefficient is calculated by optimizing processing for minimizing an index of a position gap of the one of the two frames of DWI data or the one of the two frames of the image data from the other using the coordinate conversion coefficient as a parameter.

So far, an example has been explained for acquiring two frames of DWI data corresponding to b-values having a same absolute value and the opposite signs so that the strain correction part 41B can calculate a strain correction coefficient for one of the two frames of DWI data based on the two frames of DWI data. However, the strain correction part 41B can also calculate a strain correction coefficient based on DWI data, for which MPG pulse is applied in a same axis as that for DWI data to be a target of the correction, corresponding to a b-value having a different absolute value from that of a b-value corresponding to the DWI data to be the target of the correction. Here, an example will be explained for acquiring frames of DWI data corresponding to b-values having mutually different absolute value so that the strain correction part 41B can calculate a strain correction coefficient corresponding to a b-value larger than a reference b-value based on a strain correction coefficient corresponding to the reference b-value.

More specifically, a strain correction coefficient K(b) corresponding to each b-value can be calculated based on a relational expression K(b)=f(b) between a b-value and a strain correction coefficient K(b). Coefficients of the relational expression can be acquired based on the number of reference b-values ($b_{ref}$) corresponding to the number of the coefficients and strain correction coefficients $K_{ref}$ corresponding to the reference b-values ($b_{ref}$).

The relational expression between b-values and strain correction coefficients K(b) can be approximated by an arbitrary function such as a high order expression, an exponential function or a logarithmic function. A kind of function appropriate for the approximation and whether each term more than one order is negligible or not, in case of approximation with high order expression, depend on a method for designing MPG pulses, such as which one of amplitudes, application periods or both amplitudes and application periods of MPG pulses are controlled to adjust a b-value.

For that reason, an approximate expression to express a relation between the b-values and the strain correction coefficients K(b) can be determined in advance by a simulation under conditions for MPG pulses, test imaging using a phantom at apparatus setting or designing MPG pulses, or image processing of image data acquired by a pre-scan with applying MPG pulses.

In case where the b-value can be regarded to be in direct proportion to the strain correction coefficient, strain correction coefficients K(b) corresponding to respective b-values can be calculated based on a strain correction coefficient $K_{ref}$ corresponding to a b-value ($b_{ref}$) as a reference for one pair as shown by the expression (2).

$$K(b)=(K_{ref}/b_{ref})b \qquad (2)$$

The reference b-value ($b_{ref}$) is preferably set to a small value which is not zero and can be set as an imaging condition of DWI in view of calculating strain correction coefficients K(b) corresponding to respective b-values accurately using a strain correction coefficient $K_{ref}$ corresponding to a DWI showing a small strain as a reference. That is, a strain correction coefficient corresponding to a larger b-value can be estimated based on a strain correction coefficient corresponding to a smaller b-value. For example, in case of acquiring image data corresponding to b=0 and frames of DWI data corresponding to b=500 and b=1000, a strain correction coefficient corresponding to DWI data acquired as b=1000 can be calculated according to the expression (2) based on a strain correction coefficient corresponding to DWI data acquired as b=500.

The strain correction coefficient $K_{ref}$ corresponding to the reference b-value ($b_{ref}$) can be obtained based on two frames of DWI data $I_{b+ref}$ and $I_{b-ref}$ corresponding to b-values ($+b_{ref}$, $-b_{ref}$) having the different signs or the set of the two frames of DWI data $I_{b+ref}$ and $I_{b-ref}$ corresponding to the b-values ($+b_{ref}$, $-b_{ref}$) having the different signs and the reference image data $I_{b0}$ corresponding to the b-value of zero as mentioned above with referring to FIG. 5, FIG. 6 and FIG. 7.

Alternatively, the strain correction coefficient $K_{ref}$ corresponding to the reference b-value ($b_{ref}$) may be obtained based on DWI data $I_{bref}$ corresponding to a b-value ($b_{ref}$) having a single sign of the positive or negative sign and the reference image data $I_{b0}$ corresponding to the b-value of zero. In this case, the strain correction coefficient $K_{ref}$ corresponding to the reference b-value ($b_{ref}$) can be obtained as a coordinate conversion coefficient by optimizing calculation for minimizing the sum of square differences in pixel values of binarized DWI data $I'_{bref}$ derived by binarizing the DWI data $I_{bref}$ from binarizing reference image data $I'_{b0}$ using the coordinate conversion coefficient of the binarized DWI data $I'_{bref}$ as a parameter.

The strain correction coefficient calculated in the strain correction part 41B in this way can be stored in the strain coefficient storage part 44. That is, strain correction coefficients corresponding to respective application axes and b-values of MPG pulses can be stored in the strain coefficient storage part 44. Then, the strain correction part 41B can read and acquire a strain correction coefficient corresponding to imaging conditions of DWI from the strain coefficient storage part 44. Alternatively, a function itself to calculate strain correction coefficient based on a b-value or coefficients of the function may be stored in the strain coefficient storage part 44. Then, a strain correction coefficient can be calculated according to a b-value.

Accordingly, a strain correction coefficient can be calculated based on a DWI acquired by a test imaging using a phantom or past imaging to store the calculated strain correction coefficient in the strain coefficient storage part 44. Then, the strain correction part 41B can acquire a strain correction coefficient by only referring to the strain coefficient storage part 44. As a result, processing for calculating a strain correction coefficient by the strain correction part 41B can be omitted at each imaging.

The image processing part 41C has a function to perform necessary image processing, for image displaying, of image data generated in the data processing unit 41 or image data read from the image data storage part 43 and a function to display image data for displaying after image processing on the display unit 34.

For example, the second averaging processing for frames of DWI data after the strain correction may be performed, as needed. Herewith, DWI data, after the strain correction, having a SNR necessary for diagnosis can be obtained.

The first averaging processing executed in the image reconstruction part 41A is applied to DWI data before a strain correction. Therefore, the targets of the first averaging processing are assumed to be frames of DWI data, showing an equivalent amount of strain, corresponding to a same application axis and a same b-value of MPG pulses.

On the other hand, the second averaging processing is performed to frames of DWI data after the strain correction. Accordingly, the second averaging processing can be performed to frames of DWI data corresponding to mutually different b-values. For that reason, in case of generating DWI data by image reconstruction processing using absolute values of MR signals as signal values, the second averaging processing is preferably performed to frames of DWI data corresponding to mutually different b-values like b-values having a same absolute value and mutually opposite polarity. Herewith, DWI data additionally acquired to calculate a strain correction coefficient can be utilized for improving a SNR.

That is, even when DWI data corresponding to a b-value which is not necessary for diagnosis has been acquired for calculating a strain correction coefficient, the DWI data can be used to acquire a SNR necessary for diagnostic DWI data. As a result, the number of frames of DWI data, which become addition targets for obtaining the necessary SNR, corresponding to b-values necessary for diagnosis can be decreased.

Meanwhile, when DWI data corresponding to a b-value needed for diagnosis has been acquired in order to calculate a strain correction coefficient, the DWI data can be directly used for generating DWI data for the diagnosis. In other words, DWI data originally acquired for a diagnosis can be utilized as DWI data for calculating a strain correction coefficient.

Therefore, a substantial increase in a data acquisition time and a data acquisition amount due to calculating a strain correction coefficient in the strain correction part 41B as mentioned above can be avoided. In other words, an improving rate of SNR per unit data acquisition time can be constant.

The second averaging processing may be executed to frames of DWI data of which MPG pulse have a same application direction and a same b-value. In addition, one or both of the first and the second averaging processing may not be executed. Therefore, averaging processing may be executed for averaging at least one of predetermined frames of DWI data before and after a strain correction.

Then, by the magnetic resonance imaging apparatus 20 having above mentioned configuration, DWI can be performed with applying MPG pulses corresponding to different b-values and having a same application axis to acquire frames of DWI data corresponding to the different b-values.

Next, the operation and action of the magnetic resonance imaging apparatus 20 will be described. Firstly, a case of DWI, with calculation processing of a strain correction coefficient by the magnetic resonance imaging apparatus 20, will be described.

Figure 8:
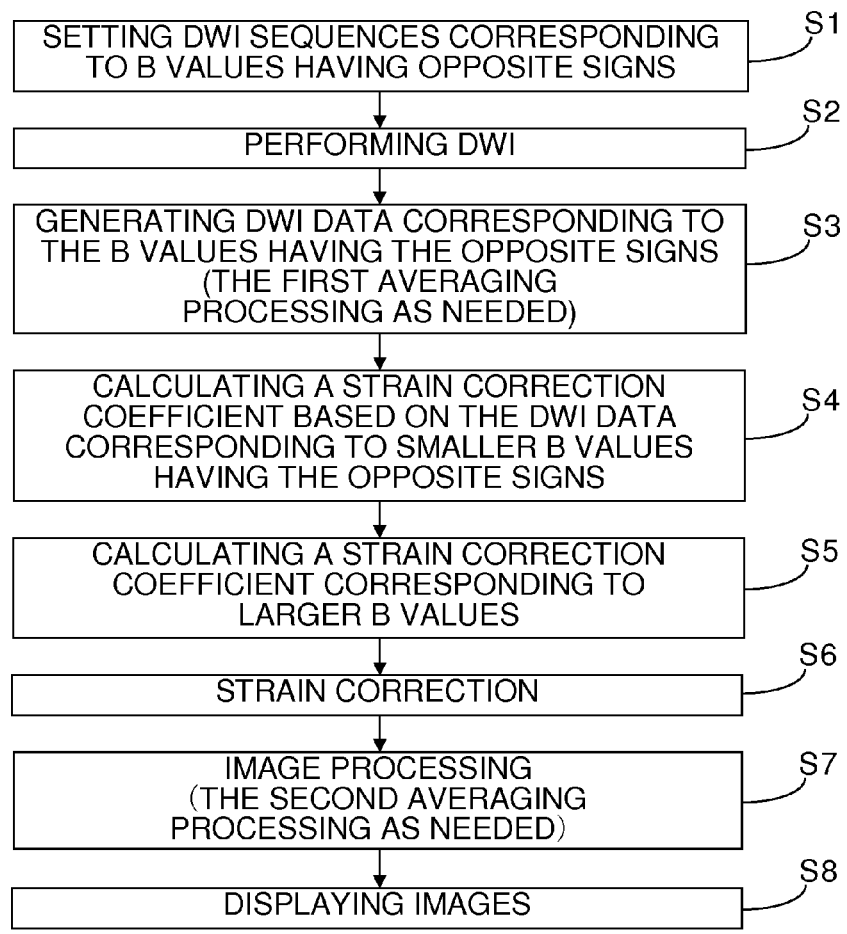
FIG. 8 a flowchart showing a flow for DWI with calculation processing of a strain correction coefficient by the magnetic resonance imaging apparatus shown in FIG. 1 is.

FIG. 8 is a flowchart showing a flow for DWI with calculation processing of a strain correction coefficient by the magnetic resonance imaging apparatus 20 shown in FIG. 1.

Firstly in step S1, the imaging condition setting part 40 sets a DWI sequence corresponding to necessary b-values according to a diagnostic purpose and an EPI sequence of which b-value is zero as shown in FIG. 3 based on the information entered from the input device 33. Further, the imaging condition setting part 40 sets a DWI sequence corresponding to a b-value having a same absolute value and an opposite sign with the smallest b-value. More specifically, as shown in FIG. 4, imaging conditions including at least two DWI sequences with an application of MPG pulses having a same application direction and having the mutually opposite polarities are set in the imaging condition setting part 40. In addition, the respective AVERAGE numbers for the first and the second averaging processing to be required in order to determine the frequencies of acquisition and addition of DWI data are set as imaging conditions, as needed.

Here, two frames of DWI data corresponding to b=500 and b=1000 are assumed to be necessary for a diagnosis, for example. In this case, EPI sequences and DWI sequences corresponding to b=0, b=+500, b=−500 and b=1000 are set.

In addition, if an AVERAGE number of the first averaging processing for frames of DWI data having a same b-value is 2, the order of sequences is set in an order of an EPI sequence corresponding to b=0, a DWI sequence corresponding to the first AVERAGE of b=+500, a DWI sequence corresponding to the first AVERAGE of b=−500, a DWI sequence corresponding to the first AVERAGE of b=1000, a DWI sequence corresponding to the second AVERAGE of b=+500, a DWI sequence corresponding to the second AVERAGE of b=−500 and a DWI sequence corresponding to the second AVERAGE of b=1000.

Next, in step S2, an imaging scan including DWI scans is performed according to the imaging conditions set by the imaging condition setting unit 40.

For that purpose, an object P is set to the bed 37 in advance, and a static magnetic field is generated at an imaging area of the magnet 21 (a superconducting magnet), for static magnetic field, excited by the static-magnetic-field power supply 26. Further, the shim-coil power supply 28 supplies current to the shim coil 22, thereby uniformizing the static magnetic field generated at the imaging area.

Subsequently, the EPI sequences set as the imaging conditions are supplied from the imaging condition setting unit 40 to the sequence controller 31 sequentially. Then, the sequence controller 31 drives the gradient power supply 27, the transmitter 29, and the receiver 30 in accordance with the pulse sequences, thereby generating gradient magnetic fields at the imaging area having the set object P, and further generating RF signals from the RF coil 24.

Consequently, the RF coil 24 receives MR signals generated due to nuclear magnetic resonance in the object P. Then, the receiver 30 receives the MR signals from the RF coil 24 and generates raw data which is digital data of the MR signals by A/D (analog to digital) conversion subsequently to necessary signal processing. The receiver 30 supplies the generated MR signals to the sequence controller 31. The sequence controller 31 outputs the MR signals to the data processing unit 41 of the computer 32.

Then, the data processing unit 41 arranges the MR signals as k-space data in the k-space formed in the k-space data storage part 42. As a result, in the k-space data storage part 42, the pieces of k-space data corresponding to b=0, the first AVERAGE of b=+500, the first AVERAGE of b=−500, the first AVERAGE of b=1000, the second AVERAGE of b=+500, the second AVERAGE of b=−500 and the second AVERAGE of b=1000 are written and stored subsequently.

Next, in step S3, the image reconstruction part 41A reads the k-space data from the k-space data storage part 42 to reconstruct image data by image reconstruction processing of the k-space data. As a result, reference image data, which is not DWI data, corresponding to b=0, two frames of DWI data corresponding to the first AVERAGE and the second AVERAGE of b=+500, two frames of DWI data corresponding to the first AVERAGE and the second AVERAGE of b=−500 and two frames of DWI data corresponding to the first AVERAGE and the second AVERAGE of b=1000 are generated respectively.

In addition, the image reconstruction part 41A generates AVERAGE image data by the first averaging processing for adding the frames of DWI data acquired with setting the same b-value and the same application axis of MPG pulses. Specifically, adding the two frames of DWI data corresponding to the first AVERAGE and the second AVERAGE of b=+500, adding the two frames of DWI data corresponding to the first AVERAGE and the second AVERAGE of b=−500 and adding the two frames of DWI data corresponding to the first AVERAGE and the second AVERAGE of b=1000 are performed in the image reconstruction part 41A. As a result, three frames of DWI AVERAGE data corresponding to b=+500, b=−500 and b=1000 are generated respectively.

Next, in step S4, the strain correction part 41B calculates a strain correction coefficient corresponding to a small b-value based on two frames of DWI AVERAGE data having the small b-value and the opposite signs. More specifically, the strain correction part 41B calculates the strain correction coefficient corresponding to b=500 based on the two frames of DWI data corresponding to b=±500.

The strain correction coefficient can be calculated by optimizing processing using parameters as coordinate conversion coefficients corresponding to one or both of the frames of binarized DWI AVERAGE data corresponding to b=+500 and b=−500 after binarizing processing as shown in FIG. 5, FIG. 6 or FIG. 7.

In case where the strain correction coefficient is calculated by the way shown in FIG. 5 or FIG. 6, the binarized reference image data corresponding to b=0 after binarizing processing is also used. Then, in case where the strain correction coefficient is calculated by the way shown in FIG. 5, a minimized target in the optimizing processing is set as the sum of square differences in pixel values of the binarized DWI AVERAGE data corresponding to each of b=+500 and b=−500 from the binarized reference image data.

Meanwhile, in case where the strain correction coefficient is calculated by the way shown in FIG. 6, a minimized target in the optimizing processing is set as the sum of square differences in pixel values of binarized DWI AVERAGE data corresponding to b=+500 from each of the binarized reference image data and the binarized DWI AVERAGE data corresponding to b=−500.

Alternatively, in case where the strain correction coefficient is calculated by the way shown in FIG. 7, a minimized target in the optimizing processing is set as the sum of square differences in pixel values of the binarized DWI AVERAGE data corresponding to b=−500 from the binarized DWI AVERAGE data corresponding to b=+500.

The strain correction coefficient calculated by the optimizing processing as mentioned above is calculated based on the DWI data, of which strain directions are mutually opposite, corresponding to b=±500. Therefore, the strain correction coefficient becomes more accurate than that calculated by optimizing processing for minimizing the sum of square differences in respective pixel values of the binarized DWI AVERAGE data corresponding to b=+500 from binarized reference image data.

Next in step S5, the strain correction part 41B calculates a strain correction coefficient corresponding to a larger b-value based on a strain correction coefficient corresponding to a smaller b-value. More specifically, the strain correction part 41B assumes a strain correction coefficient to be proportional to a b-value, and then calculates the strain correction coefficient corresponding to b=1000 based on the strain correction coefficient corresponding to b=500 by the expression (2).

By this way, the strain correction coefficients corresponding to all the b-values set as the imaging conditions can be easily acquired. The acquired strain correction coefficients for the respective b-values can be written and stored in the strain coefficient storage part 44, as needed.

Next, in step S6, the strain correction part 41B performs the strain correction for each frame of the DWI AVERAGE data by using a strain correction coefficient corresponding to each b-value. More specifically, strains of the frames of the DWI AVERAGE data corresponding to b=500 and b=1000 are corrected using the strain correction coefficients corresponding to b=500 and b=1000 respectively.

Next, in step S7, the image processing part 41C performs image processing, necessary for an image display, of the image data corresponding to b=0 and the DWI AVERAGE data after the strain correction. For example, the second averaging processing can be performed among the frames of the DWI AVERAGE data, after the strain correction, corresponding to different b-values. In this example case, the two frames of the DWI data corresponding to b=500 and b=1000 are needed for diagnosis while the DWI AVERAGE data corresponding to b=−500 is not required for the diagnosis. For that reason, the second averaging processing can be performed to the frames of the DWI AVERAGE data corresponding to b=±500. Herewith, the DWI AVERAGE data, for a diagnosis, corresponding to b=500 and improved in SNR can be generated.

Next, in step S8, the image processing part 41C displays the image data corresponding to b=0 and the DWI AVERAGE data for display, after image processing, on the display unit 34. Herewith, a user can confirm an image corresponding to b=0, a DWI corresponding to b=500 and a DWI corresponding to b=1000 displayed on the display unit 34.

At this time, the DWIs displayed on the display unit 34 become images of which strains have been corrected satisfactorily since the DWIs have been strain-corrected based on the strain correction coefficients calculated with a high accuracy. In addition, the DWIs displayed on the display unit 34 become images each having an improved SNR by the first and the second averaging processing.

Next, a case of DWI, with strain correction processing using a strain correction coefficient acquired in advance by the magnetic resonance imaging apparatus 20, will be described.

Figure 9:
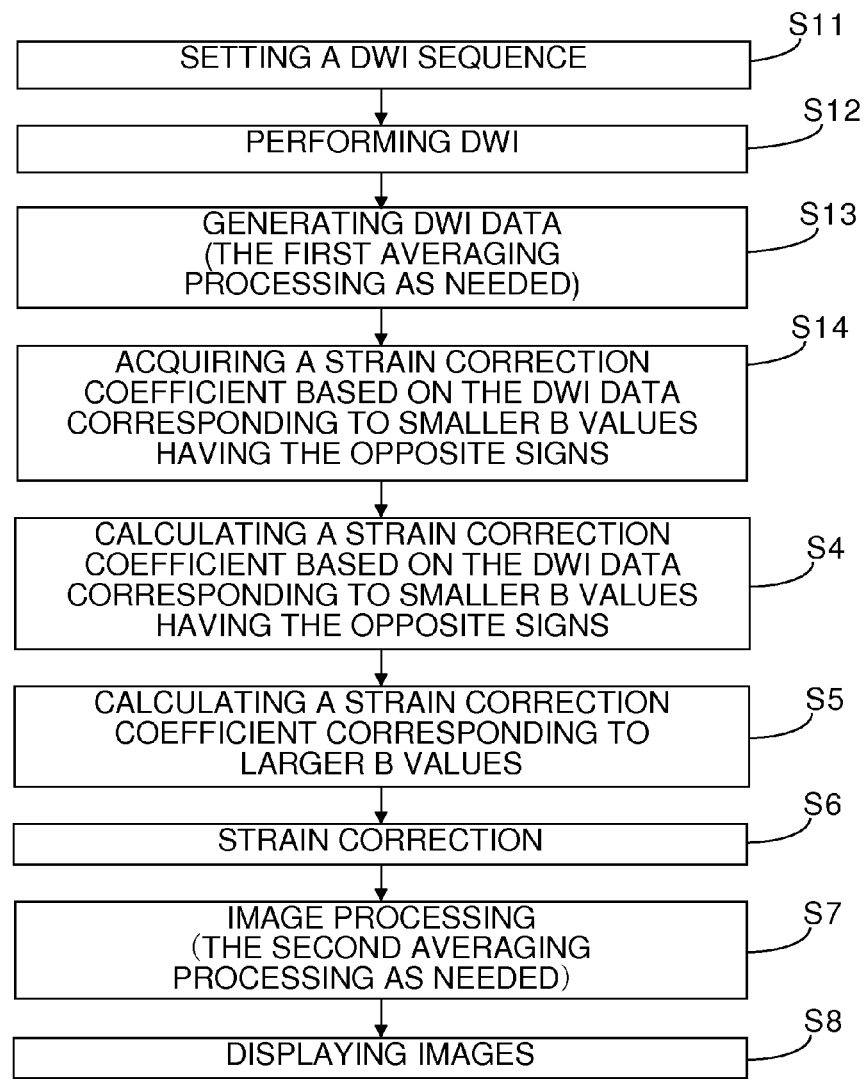
FIG. 9 is a flowchart showing a flow for DWI with strain correction processing using a strain correction coefficient acquired in advance by the magnetic resonance imaging apparatus shown in FIG. 1.

FIG. 9 is a flowchart showing a flow for DWI with strain correction processing using a strain correction coefficient acquired in advance by the magnetic resonance imaging apparatus 20 shown in FIG. 1. Note that, each step similar to a step in the flowchart shown in FIG. 8 is assigned with the same sign and description thereof is omitted.

Firstly, strain correction coefficients acquired by test imaging using a phantom or past imaging are stored in the strain coefficient storage part 44 in advance. However, each of the strain correction coefficients is calculated by optimizing processing using a parameter as a coordinate conversion coefficient based on two flames of DWI AVERAGE data corresponding to b-values having a same absolute value and the mutually opposite signs as shown in FIGS. 5, 6 and 7. In addition, for calculating the strain correction coefficients, DWI AVERAGE data corresponding to a small b-value which may be set as an imaging condition for DWI is used. For example, a strain correction coefficient corresponding to b=500 is stored in the strain coefficient storage part 44.

Next, in step S11, the imaging condition setting unit 40 sets DWI sequences corresponding to necessary b-values in accordance with a diagnosis purpose and an EPI sequence of which b-value is zero based on the information entered from the input device 33. In addition, an AVERAGE number of DWIs is set, as needed.

Note that, differently from step S1 in FIG. 8, it is not necessary to set DWI sequences corresponding to a b-value having a same absolute value and the opposite sign as and to that of a certain b-value. Accordingly, it is assumed that EPI sequences corresponding to b=0, b=500 and b=1000 are set, for example.

Next, in step S12, according to the imaging conditions set in the imaging condition setting unit 40, an imaging scan including DWI scans is performed. More specifically, pieces of k-space data corresponding to b-values (b=0, 500 and 1000) having mutually different absolute values respectively are acquired in a flow similar to step S1 in FIG. 8.

Next, in step S13, the image reconstruction part 41A generates image data and frames of DWI data corresponding to the b-values (b=0, 500 and 1000) having the mutually different absolute values respectively. For that purpose, not only the image reconstruction processing of the k-space data but also the first averaging processing of the DWI data according to the AVERAGE number set as the imaging condition are performed. When the first averaging processing has been performed, DWI AVERAGE data is generated.

Next, in step S14, the strain correction part 41B acquires a strain correction coefficient, corresponding to a small b-value, calculated based on two frames of DWI data or DWI AVERAGE data corresponding to a small b-value and the opposite signs, from the strain coefficient storage part 44. That is, the strain correction part 41B acquires the strain correction coefficient corresponding to b=500 from the strain coefficient storage part 44.

Consequently, in step S5, the strain correction part 41B becomes possible to calculate the strain correction coefficient corresponding to b=1000 based on the strain correction coefficient corresponding to b=500. Then, images derived by necessary image processing of DWIs after the strain correction using the strain correction coefficients can be displayed on the display unit 34.

As described above, the magnetic resonance imaging apparatus 20 is an apparatus configured to acquire two frames of DWI data having the opposite strain polarities by diffusion imaging with applying MPG pulses having a same application axis, a same absolute value of b-value and the opposite polarities to calculate a strain correction coefficient with high accuracy based on the two frames of the DWI data having the opposite polarities.

Accordingly, by the magnetic resonance imaging apparatus 20, a DWI of which strain is corrected with higher accuracy than before can be obtained. Especially, no diffusing nerve fascicle travels only in limited directions in an abdominal part of an object P. Therefore, in case of acquiring DWIs with setting an abdominal part as an imaging part, DWIs of which strains are successfully corrected can be acquired by calculating strain correction coefficients with higher accuracy with setting application axes of MPG pulses to one axis direction. On the other hand, even if application axes of MPG pulses are different directions, strain correction coefficients can be calculated with higher accuracy by applying MPG pulses having the opposite polarities for each application axis.

In addition, by the magnetic resonance imaging apparatus 20, based on a strain correction coefficient corresponding to a certain b-value, a strain correction coefficient corresponding to another b-value can be calculated. Consequently, an amount of data processing needed for calculating a strain correction coefficient can be reduced.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A magnetic resonance imaging apparatus comprising: an imaging unit configured to acquire frames of diffusion weighted image data corresponding to different b-values by diffusion weighted imaging with applying MPG pulses corresponding to the different b-values of which application axes are same; and
   a strain correction unit configured to calculate a strain correction coefficient for first diffusion weighted image data based on second diffusion weighted image data to generate image data by a strain correction of the first diffusion weighted image data using the calculated strain correction coefficient,
   the second diffusion weighted image data being acquired while applying an MPG pulse whose polarity is opposite to the polarity of an MPG pulse used while acquiring the first diffusion weighted image data, the first diffusion weighted image data and the second diffusion weighted image data being among the frames of the diffusion weighted image data.

2. A magnetic resonance imaging apparatus of claim 1, wherein said imaging unit is configured to acquire two frames of diffusion weighted image data corresponding to b-values having a same absolute value and mutually opposite signs; and
said strain correction unit is configured to calculate a strain correction coefficient corresponding to one of the two frames of the diffusion weighted image data based on the two frames of the diffusion weighted image data.

3. A magnetic resonance imaging apparatus of claim 1, wherein said imaging unit is configured to acquire frames of diffusion weighted image data corresponding to b-values having different absolute values; and
said strain correction unit is configured to calculate a strain correction coefficient corresponding to a larger b-value than a reference b-value based on a strain correction coefficient corresponding to the reference b-value.

4. A magnetic resonance imaging apparatus of claim 1, further comprising:
a storage unit configured to store the strain correction coefficient calculated by said strain correction unit,
wherein said strain correction unit is configured to acquire the strain correction coefficient in reference to the storage unit.

5. A magnetic resonance imaging apparatus of claim 2, wherein said imaging unit is configured to acquire image data with setting a b-value to zero further; and
said strain correction unit is configured to calculate the strain correction coefficient based on the image data acquired with setting the b-value to zero.

6. A magnetic resonance imaging apparatus of claim 2, wherein said strain correction unit is configured to calculate respective coordinate conversion coefficients for the two frames of the diffusion weighted image data or two frames of image data generated based on the two frames of the diffusion weighted image data by optimizing processing for minimizing an index of a position gap of each of the two frames of the diffusion weighted image data or each of the two frames of the image data from image data acquired with setting a b-value to zero to adopt a coordinate conversion coefficient corresponding to a smaller index as the strain correction coefficient, the respective coordinate conversion coefficients being used as parameters for the optimizing processing.

7. A magnetic resonance imaging apparatus of claim 2, wherein said strain correction unit is configured to determine the strain correction coefficient based on a coordinate conversion coefficient for one of the two frames of the diffusion weighted image data or one of two frames of image data generated based on the two frames of the diffusion weighted image data, the coordinate conversion coefficient being calculated by optimizing processing for minimizing an index of a position gap of the one of the two frames of the diffusion weighted image data or the one of the two frames of the image data from image data acquired with setting a b-value to zero and an index of a position gap of that from an other using the coordinate conversion coefficient as a parameter.

8. A magnetic resonance imaging apparatus of claim 2, wherein said strain correction unit is configured to determine the strain correction coefficient based on a coordinate conversion coefficient for one of the two frames of the diffusion weighted image data or one of two frames of image data generated based on the two frames of the diffusion weighted image data, the coordinate conversion coefficient being calculated by optimizing processing for minimizing an index of a position gap of the one of the two frames of the diffusion weighted image data or the one of the two frames of the image data from an other using the coordinate conversion coefficient as a parameter.

9. A magnetic resonance imaging apparatus of claim 2, wherein said strain correction unit is configured to calculate the strain correction coefficient by processing including edge detection of the two frames of the diffusion weighted image data.

10. A magnetic resonance imaging apparatus of claim 1, further comprising:
an image processing unit configured to execute an averaging processing for averaging at least one of predetermined frames of diffusion weighted image data before the strain correction and predetermined frames of diffusion weighted image data after the strain correction.

11. A magnetic resonance imaging apparatus of claim 10, wherein said image processing unit is configured to perform the averaging processing of frames of diffusion weighted image data corresponding to mutually different b-values after the strain correction.

12. A magnetic resonance imaging method comprising:
acquiring frames of diffusion weighted image data corresponding to different b-values by diffusion weighted imaging with applying MPG pulses corresponding to the different b-values of which application axes are same; and
calculating a strain correction coefficient for first diffusion weighted image data based on second diffusion weighted image data to generate image data by a strain correction of the first diffusion weighted image data using the calculated strain correction coefficient,
the second diffusion weighted image data being acquired while applying an MPG pulse whose polarity is opposite to the polarity of an MPG pulse used while acquiring the first diffusion weighted image data, the first diffusion weighted image data and the second diffusion weighted image data being among the frames of the diffusion weighted image data.

\* \* \* \* \*